United States Patent

Wang et al.

[11] Patent Number: 5,902,631
[45] Date of Patent: May 11, 1999

[54] LUBRICITY GRADIENT FOR MEDICAL DEVICES

[76] Inventors: Lixiao Wang, 12822 86th Pl. North, Maple Grove, Minn. 55369; Irina Nazarova, 2610 Queensport Rd., Woodbury, Minn. 55125

[21] Appl. No.: 08/868,301

[22] Filed: Jun. 3, 1997

[51] Int. Cl.[6] ........................ B05D 3/10
[52] U.S. Cl. ................ 427/2.1; 428/212; 428/413; 428/474.4; 428/522; 427/2.12; 427/340; 604/265
[58] Field of Search ............ 604/265; 427/2.12, 427/340, 2.1; 428/212, 413, 522, 474.4

[56] References Cited

U.S. PATENT DOCUMENTS

| | | | |
|---|---|---|---|
| 2,814,296 | 11/1957 | Everett | 604/265 |
| 3,566,874 | 3/1971 | Shepherd | 128/349 |
| 3,826,674 | 7/1974 | Schwarz | 117/62.2 |
| 4,026,296 | 5/1977 | Stoy et al. | 128/349 |
| 4,100,309 | 7/1978 | Micklus et al. | 427/2 |
| 4,248,685 | 2/1981 | Beede et al. | 204/159.22 |
| 4,373,009 | 2/1983 | Winn | 428/424.2 |
| 4,447,590 | 5/1984 | Szycher | 528/76 |
| 4,459,318 | 7/1984 | Hyans | 427/36 |
| 4,588,398 | 5/1986 | Daugherty et al. | 604/265 |
| 4,876,126 | 10/1989 | Takemura et al. | 428/35.7 |
| 5,041,100 | 8/1991 | Rowland et al. | 604/265 |
| 5,091,205 | 2/1992 | Fan | 427/2 |
| 5,135,516 | 8/1992 | Sahatjian et al. | 604/265 |
| 5,229,211 | 7/1993 | Murayama et al. | 428/424.4 |
| 5,441,488 | 8/1995 | Shimura | 604/265 |
| 5,503,631 | 4/1996 | Onishi et al. | 604/96 |
| 5,509,899 | 4/1996 | Fan et al. | 604/96 |
| 5,531,715 | 7/1996 | Engelson et al. | 604/265 |
| 5,670,558 | 9/1997 | Onishi et al. | 523/112 |
| 5,693,034 | 12/1997 | Buscemi | 604/265 |

FOREIGN PATENT DOCUMENTS

| | | | |
|---|---|---|---|
| 0 380 102 | 8/1990 | European Pat. Off. | A61M 29/02 |
| 91/08790 | 6/1991 | WIPO | A61M 25/00 |

OTHER PUBLICATIONS

Solomons, Organic Chemistry, 6th Ed, John Wiley & Son, Inc. 1996.
Tecoflex™ product literature.
Gantrez™ An Copolymer pp.1–13;1995.
M. Szycher, Blood Compatible Materials and Devices Perspectives Towards the 21st Century, C. P. Sharma and M. Szycher eds.

*Primary Examiner*—Robert Dawson
*Assistant Examiner*—Caixia Lu-Rutt

[57] ABSTRACT

A medical device for partial insertion into a patient and navigating passageways, channels, canals, cavities, and other interior parts of said patient, said medical device comprising an elongate body having an in the body segment which, in normal use, is inserted in the body of a patient. At least a portion of the in-the-body segment is provided with a lubricious coating. The coating displays a gradient of lubricity along the length of thereof.

28 Claims, 1 Drawing Sheet

LUBRICITY GRADIENT FOR MEDICAL DEVICES

BACKGROUND OF THE INVENTION

1. Field of the Invention

This invention relates to a medical devices which have a segment which is inserted into the body and a segment which is retained outside the body for manipulation. In particular it relates to such structures in which the a portion of the in-the-body segment is coated with a lubricious coating material.

2. Description of the Related Art

Medical devices, such as catheters and guide wires, designed to navigate the passageways, channels, canals, cavities, and other interior parts of a patient, serve a variety of purposes including the delivery of biologically compatible fluids to a site within the body, such as radiologically opaque fluid for contrast x-rays, the delivery of a stent to a desired location within the body, the delivery of a balloon to a desired location to widen a vessel and the delivery of a fiber optic cable to a desired location.

These applications require smooth devices exhibiting a certain degree of lubricity so as to avoid injuring the mucous membranes and other bodily parts with which they come in contact. Depending on the intended use of such a device, the requirements for lubricity along the surface of the device may vary widely. In the case of balloon catheters, it is desirable for the balloon to have a lubricating portion and a non-lubricating portion to avoid the so-called 'watermelon seed' problem wherein a balloon which is too lubricious shoots forward on inflation. To this end, U.S. Pat. No. 5,503,631 Onishi et al. discloses a vasodilating catheter balloon whose body has a lubricating portion and a non-lubricating portion. The lubricious property of the balloon is created by grafting a lubricious coating onto a non-lubricious substrate.

U.S. Pat. No. 3,826,674 to Schwarz discloses a lubricious coating based on a hydrophilic polyurethane foam where the lubricity is imparted through the use of an anhydride coating. Schwarz further discloses that the anhydride can be made more hydrophilic via treatment with a low molecular weight amine.

U.S. Pat. No. 4,876,126 to Takemura et al discloses a medical instrument that exhibits low frictional resistance when wetted with aqueous solutions e.g. body fluids. The instrument is prepared by treating a substrate with a solution containing a reactive functional group to form an undercoat and then treating the substrate with a water soluble polymer such as a maleic anhydride polymer to covalently bond the reactive functional group with the water soluble polymer. The water soluble polymers disclosed are chain structured, non-cross-linked polymers having a hydrophilic group.

U.S. Pat. No. 5,229,211 discloses a medical device with a reduced lubricity on the out-of-body end to aid in manipulating the device from outside the body. This reduced lubricity is achieved by treating the basal part with an isocyanate prepolymer to reduce hydrophilicity relative to the proximal part of the device.

U.S. Pat. No. 5,441,488 to Shimura et al discloses a medical device having a lubricious surface in a wetted state. The device comprises a substrate and water-swellable polymer coating. The coating is bonded via a reaction between a functional group on the coating (e.g. a hydroxy, amino or epoxy group) and an acid anhydride group or proton donating group on the surface.

SUMMARY OF THE INVENTION

It has now been discovered that significant advantages are provided by providing a coating of varied lubricity on an in-the-body segment of elongated transcutaneous medical instruments such as guide wires, catheters, fiber optic devices, and the like. By varying the lubricity of a lubricious coating, portions of the device greater can be tailored for specific problems allowing greater control over the device properties.

In one aspect the invention is a medical device adapted for insertion into the body of a patient and minipulation from outside the body, the device comprising an elongate body extending between proximal and distal ends of the device, the distal end, when the device is in use, being inserted into the body of the patient, the proximal end, when the device is in use, remaining outside of the body of the patient, the elongate body between the distal end and the proximal end having an in-the-body segment which, when the device is in use, will normally be positioned within the body of the patient and an out-of-the body segment near the proximal end which, when the device is in use, will normally remain outside of the body of the patient, the in-the-body segment having on at least a portion thereof a coating material which, exhibits a gradient of lubricity along the length of said in-the-body segment portion.

The lubricity gradient may be provided by modification or overcoating of the lubricious coating material.

DESCRIPTION OF THE PREFERRED EMBODIMENTS

Figure 1:
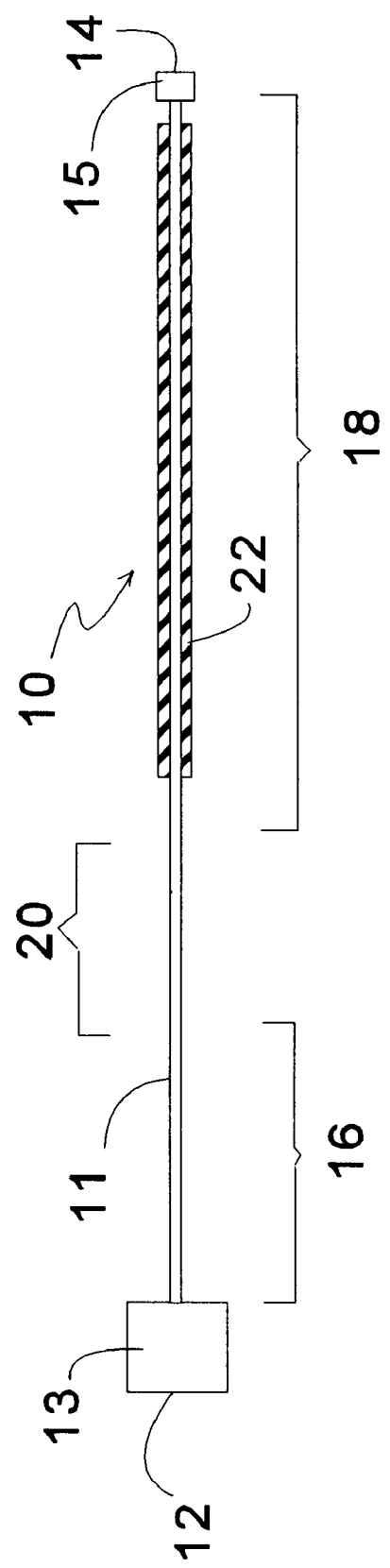
FIG. 1 is a schematic representation of an elongated medical device of the invention.

Referring to FIG. 1 there is shown an elongated medical device 10 for insertion into a patient which may be a guide wire, catheter, cannula, fiber optic device or the like. Device 10 extends between proximal end 12 and distal end 14 and includes an elongate body 11. A control mechanism 13 may optionally be provided at or near the proximal end of device 10 to facilitate manipulation of the device and/or activation of functional structure provided on the device, such a drug delivery or balloon inflation structure. Device 10 may also optionally be provided with a functional structure 15, such as an inflatable balloon, deployable stent, drug delivery mechanism, or the like, typically at or near the distal end 14.

Near the proximal end of body 11 is an out-of-body segment 16 which, in ordinary use, remains outside of the patient. Another segment of body 11, in-the-body segment 18, extends proximally from the distal end. In ordinary use of the device, in-the-body segment 18 is inserted into the body of the patient. A third segment 20, between segments 16 and 18, may vary between in-the-body and out-of-body locations depending on the procedure employed and the patient's anatomy.

Very little limitation, is placed on the material for the elongate body 11. Most devices will have a relatively flexible body, such as when device 10 is a catheter or guide wire. However, the invention may also be used with inflexible transcutaneous devices such as a needle. Body 11 may be made of organic high polymer materials such as polyamide, polyester, polyvinyl chloride, polystyrene, polyacrylate, polymethacrylate, polyacrylonitrile, polyacrylamide, polyethylene, polypropylene, polyurethane, polyvinyl acetate, silicone resins, and copolymers and blends thereof. However, various of inorganic materials such as glass, ceramic, stainless steel, and a super elastic metal or shape memory alloy such as Ni—Ti alloy, and the like may be employed in part or all of body 11. Body 11 may also be formed as a laminate of different materials. Depending on the nature of the specific device 10, body 11 may be provided with one or more lumens, electrical connectors, optical fibers or the like, as is well known in the medical device art.

One specific embodiment of device 10 is a balloon catheter for angioplasty and the like, in which case functional structure 15 will include an inflatable balloon, located very near the distal end of device 10; the elongate body 11 will be a flexible tube, typically polymeric, containing at least an inflation fluid lumen for the balloon; and a control mechanism 13 of conventional design will be provided for manipulating the catheter to the desired site in the body and for causing the balloon to inflate and deflate as desired. Such a catheter may also be provided with a soft distal tip as part of functional structure 15 to facilitate maneuvering the balloon to cross a lesion and/or a guide wire lumen to allow the catheter to be inserted over a guide wire. Another specific embodiment of device 10 is a guide wire in which case body 11 may be a metal wire, there may not be any control mechanism 13 present at the proximal end and the distal functional structure 15 may simply be a conventional coiled or soft polymeric tip.

In accordance with the present invention in-the-body segment 18 includes a coated portion 22. Portion 22 may be coextensive with segment 18 or only a fractional length of segment 18. The coating which forms portion 22 may optionally also extend over some or all of segments 20 and 16, however for purposes of this invention only portion 22 is of interest.

The essential characterizing feature of the present invention is that portion 22 displays a lubricity gradient. That is, over the length of portion 22 there is a variation in the lubricity of coating 22. This lubricity gradient may be expressed as a continuously varying lubricity over the length of portion 22 or as one or more steps of differing lubricity over the length of portion 22.

The lubricity gradient may be produced in a number of ways. In accordance with one method, portion 22 is coated with a varying thickness of coating material to produce the gradient. In another method, portion 22 is provided with a lubricious coating material and then some of the coating on portion 22 is subjected to a chemical reaction which alters the lubricity of the coating. In still another method, portion 22 is provided with a lubricious coating and then some of the coating on portion 22 is overcoated with a second coating material which displays a different lubricity. Of course, combinations of these techniques may also be used.

A gradient in lubricity can be obtained by varying the extent of reaction of the coating to a lubricity altering substance by exposing the coating to said lubricity altering substance in a manner which varies the length of time of exposure to the lubricity altering substance along the length of said in-the-body segment portion. Such variation may be continuous, for instance by dipping the entire portion 22 into a solution containing a reactive substance and then gradually and continuously withdrawing the dipped portion 22 from the proximal or distal end thereof Similarly, a continuously varied coating thickness can be obtained by dip coating portion 22 in like manner. In like manner a lubricity altering non-reactive overcoating can also be provided.

A lubricity gradient may also be formed by stepped variation. Dip methods employing incremental withdrawal or successive dips of decreasing length can be utilized to produce the gradient.

Drawing a portion of segment 18 of device 10 through a coating, a reactant or an overcoating material at a continuously or stepwise varying rate may also be used to provide a coated portion 22 characterized by a lubricity gradient. It is also possible to alter the concentration of coating, reactant or overcoating material to produce a lubricity gradient.

In one exemplary embodiment, a portion of an in-the-body segment of an elongate medical device is coated with a maleic anhydride copolymer. Examples of such copolymers include poly(ethylene-maleic anhydride) sold by Aldrich Chemical Co. maleic anhydride-methyl vinyl ether copolymers such as Gantrez® AN 169 sold by G.A.F. Corporation. With such a coating material the lubricity may be altered by differential hydrolysis of the anhydride groups of the polymer and neutralization of the resulting acid groups. This may be readily accomplished by using a high pH solution (pH about 10 or higher, suitably 10–12) using a gradual drawing, successive dipping or other technique as described above.

Another way the maleic anhydride copolymer may be modified is by partial reaction with a solution containing an anhydride or carboxylic acid reactive compound such as an amine, alcohol, epoxy or imine compound. The reactive compound may suitably be a low molecular weight monofunctional compound, in which case hydrophilicity will usually be reduced. Polyfunctional compounds which produce surface crosslinking may also be employed. Polyethylene glycols or monohydroxy derivatives thereof may also be employed. Treatment of the coating with such reactive compounds may be combined with neutralization reactions of unreacted acid groups also obtained from the specific reactions or from hydrolysis of any unreacted anhydride groups remaining after such reactions.

Carboxylic acid-containing polymers may also be used as coating materials in the invention. Copolymers of acrylic acid, methacrylic acid, maleic acid, fumaric acid or other polymerizable ethylenically unsaturated acids are examples. Such copolymers may be modified in stepwise or continuous manner as described above by partial neutralization or by reaction with acid reactive compounds, or both, to provide a lubricity gradient after coating a portion of the in-the-body segment of an elongated medical device.

In another embodiment, a hydrogel coating is provided with a lubricity gradient. For example polyethylene oxide may be captured in an interpenetrating crosslinked acrylic polymer network by polymerizing a mixture of an acrylic monomer composition comprising a monomer having plural (meth)acrylate groups and polyethylene oxide, thereby providing a hydrogel coating. The lubricity of such a coating can be modified, for instance by reaction of the active hydrogen groups of the polyethylene oxide with an active hydrogen reactive compound such as an isocyanate, an acid chloride, an anhydride, an alkyl halide, etc. Varying the ratio of monomer to polyethylene glycol over the length of the coating can also be used to create a lubricity gradient in accordance with the present invention.

In general hydrophilic lubricious coating materials are preferred as coating materials for use in the invention. However hydrophobic lubricious coating materials can be similarly provided with a gradient of lubricity and thus employed in the invention. Additional examples of hydrophilic coating materials include polyvinyl alcohol polymers and copolymers, ionomeric polymers, and polyvinyl pyrrolidone (which may optionally be mixed with polyurethane).

The invention is illustrated by the following non-limiting examples.

EXAMPLE 1

Polyethylene tubing is coated with a hydrophobic coating material which is comprised of a mixture of silicone solutions: Dow Corning 360 and Dow Corning MDX4-4159 dissolved in heptane or IPA. The ratio between two silicone fluids can vary from 5:1 to 2:1, the concentration from 2.5% to 70%, coating method can be dipping or using coating machine which draws the tubing through the coating material solution at a predetermined rate. The coating is dried and cured at 45° C., 50% RH for 0.5–6 hours, with best results obtained at 2–4 hours.

Coatings having a varied slipperiness (slip angles were from 8.1° to 4.2° along the length) were obtained using a coating machine and varying the drawing speed as a length of the tubing was drawn through the solution and thereby producing a varied coating thickness along the length of the tubing.

EXAMPLE 2

Polyurethane tubing "Tecoflex 95 A" filled with tungsten (80%–90% by weight), ground and superwashed, was coated with poly(ethylene-maleic anhydride) copolymer (MW 100,000) (Aldrich Co.) in MEK/IPA. Suitable concentrations of copolymer in the solvent mixture are from 3% to 10% and suitable MEK/IPA weight ratios are from 70/30 to 50/50, preferably 60/40. The coating was applied by a coating machine with different speeds along the length to get different thickness. The coating is dried at 50° C.–80° C., typically 70° C.(±5° C.) for 0.5–6 hours, typically ±0.2 hours after which it is sterilized (using ethylene oxide gas cycle at 47° C. at 50% RH for 15–30 hours). After wetting the coated tubing in saline solution (pH=7.4) the coating became lubricious. Different slip angles along the length of the tubing are obtained from this process with variation being as much as from 8.5° to 2.5°.

EXAMPLE 3

Polyethylene tubing is plasma treated by He plasma for 9 minutes and coated with hydrogel coating based on the solution of poly(ethylene oxide) (MW 900,000) and neopentylglycol diacrylate (PEO:NPG wt ratio 10:1) in a 4:1 mixture of IPA/water. AIBN is added as a photoinitiator. Using different coater speeds, different coating thickness are obtained. The coating solution is dried, cured by UV-light, and then sterilized (using ethylene oxide gas cycle at 47° C. at 50% RH for 15–30 hours). After wetting the coated tubing (at any pH) the coating became lubricious with different slip angles along the length (from 10.4° to 4.4°).

EXAMPLE 4

Polyurethane tubing "Tecoflex 95A" filled with tungsten (80%–90%) by weight, ground and superwashed is coated with poly(ethylene-maleic anhydride) copolymer (MW 100,000) (Aldrich Co.) in a MEK/IPA solvent mixture. Suitable concentrations of copolymer in the solvent mixture are from 2% to 10%, with 8% being preferred. Suitable MEK/IPA weight ratios are from 70/30 to 50/50, preferably 60/40. The coating is applied by a coating machine with a shallow cap. A constant draw speed is used to get a uniform coating thickness along the coated length. Approximately 10–15 minutes after passing through the coater, part of the coated length is treated with a neutralizing solution having very high pH (pH 11–13) solution (0.1N NaOH in water, or 0.1N NaOCH$_3$ in IPA) for 5–40 sec, preferably 15–30 seconds. The coating is dried at 70°±5° C. for 1±0.2 hour, sterilized (using ethylene oxide gas cycle at 47° C., at 50% RH for 15–30 hours). After wetting the coated tubing with saline solution the coating becomes lubricious with different slip angles at stepped intervals along the length. Slip angles of from 7.5 to 2.5 have been obtained from this process depending on whether the tested portion of the coating has been treated with neutralizing solution and for how long.

EXAMPLE 5

Polyurethane tubing is coated with poly(methyl vinyl ether-maleic anhydride) copolymer Gantrez AN 169 (MW 1,500,000) in MEK. The concentration is from 0.5% to 8%, preferably 5%. The coating is applied by a coating machine with a shallow cap. A constant draw speed is used to get a uniform coating thickness along the coated length. Part of the coating is then treated with an a reactive agent which is an alcohol, an epoxide, a primary amine or a secondary amine. In these cases the anhydride linkage is cleaved to form a half ester-half acid, or a half amide-half acid salt. After treatment the coating is dried and sterilized as in the previous examples. After wetting the coated tubing with saline solution (pH=7.4), the coating becomes lubricious with different slip angles at stepped intervals along the length. Slip angles of from 6.5 to 3.5 have been obtained from this process depending on whether the tested portion of the coating has been treated with reactive agent, the reactive agent employed and the extent of reaction obtained.

Those skilled in the art may recognize other equivalents to the specific embodiments described herein which equivalents are intended to be encompassed by the claims attached hereto.

We claim:

1. A medical device adapted for insertion into the body of a patient and manipulation from outside the body, the device comprising an elongate body extending between proximal and distal ends of the device, the distal end, when the device is in use, being inserted into the body of the patient, the proximal end, when the device is in use, remaining outside of the body of the patient, the elongate body between the distal end and the proximal end having an in-the-body segment which, when the device is in use, will normally be positioned within the body of the patient and an out-of-the body segment near the proximal end which, when the device is in use, will normally remain outside of the body of the patient, the in-the-body segment having on at least a portion thereof a coating material which, exhibits a gradient of lubricity along the length of said in-the-body segment portion.

2. A medical device as in claim 1 wherein said coating comprises a modified copolymer of maleic anhydride.

3. A medical device as in claim 2 wherein the lubricity gradient is created by varying the extent of hydrolysis of the maleic anhydride copolymer along the length of said elongate body in-the-body segment portion.

4. A medical device as in claim 3 wherein said hydrolysis is carried out at a high pH.

5. A medical device as in claim 2 wherein the maleic anhydride copolymer is modified to partially esterify the anhydride groups thereon, said lubricity gradient being provided by varying the proportion of esterified groups.

6. A medical device as in claim 2 wherein the maleic anhydride copolymer is modified by reaction of some of the anhydride groups thereof with a member selected from the group consisting of monofunctional amines, alcohols, epoxies, imines and mixtures thereof.

7. A medical device as in claim 1 wherein said coating comprises a hydrogel polymer.

8. A medical device as in claim 7 where said hydrogel comprises a polyethylene oxide retained within a crosslinked polymer network.

9. A medical device as in claim 8 wherein the concentration of said polyethylene oxide in said crosslinked polymer network is varied along the length of said elongate body in-the-body segment portion.

10. A medical device as in claim 1 wherein the thickness of said coating is varied along its length to create said lubricity gradient.

11. A medical device as in claim 1 wherein said coating comprises a polycarboxylic acid.

12. A medical device as in claim 1 wherein said lubricity gradient varies substantially continuously over the length of said elongate body in-the-body segment portion.

13. A medical device as in claim 1 wherein said gradient of lubricity is provided by at least one stepped change in lubricity along the length of said in-the-body segment portion.

14. A medical device as in claim 13 wherein said gradient of lubricity comprises a plurality of steps over the length of the elongate body in-the-body segment portion.

15. A medical device as in claim 1 wherein said device is a catheter.

16. A medical device as in claim 1 wherein said device is a guide wire.

17. A medical device as in claim 1 wherein said coating comprises a hydrophilic polymer.

18. A medical device as in claim 1 wherein said coating comprises a hydrophobic polymer.

19. A method for producing a medical device as in claim 1 comprising:
  coating said in-the-body segment portion with a lubricious polymeric coating material, and then
  reacting the lubricious polymeric material with a substance which alters the lubricity of the coating, the extent of reaction being varied at least once along the length of the in-the-body segment portion.

20. A method as in claim 19 wherein the extent of reaction is varied by exposing the coating to said lubricity altering substance in a manner which varies the length of time of exposure to the lubricity altering substance along the length of said in-the-body segment portion.

21. A method as in claim 20 wherein said time of exposure is continuously varied.

22. A method as in claim 20 wherein said time of exposure is varied stepwise at least once along the length of the in-the-body segment portion.

23. A method as in claim 19 wherein the extent of reaction is varied by exposing the coating to said lubricity altering substance in a manner which varies the concentration of the lubricity altering substance to which the in-the-body segment portion is exposed along the length thereof.

24. A method as in claim 19 wherein said coating material is a maleic anhydride copolymer and said lubricity altering substance is a member of the group consisting of inorganic hydroxides, water, monofunctional amines, alcohols, epoxies, imines and mixtures thereof.

25. A method for producing a medical device as in claim 1 comprising coating said in-the-body segment portion with a lubricious polymeric coating material in a manner which varies the thickness of said coating material at least once along the length of the in-the-body segment portion.

26. A method as in claim 25 wherein said coating thickness is varied by exposing the in-the-body segment portion to said lubricious polymeric coating material for a length of time which varies along the length of the in-the-body segment portion.

27. A method as in claim 25 wherein said coating thickness is varied by exposing the in-the-body segment portion to a concentration of said lubricious polymeric coating material which varies along the length of the in-the-body segment portion.

28. A medical device adapted for insertion into the body of a patient and manipulation from outside the body, the device comprising
  an elongate body extending between proximal and distal ends of the device, the distal end, when the device is in use, being inserted into the body of the patient, the proximal end, when the device is in use, remaining outside of the body of the patient,
  the elongate body between the distal end and the proximal end having an in-the-body segment which, when the device is in use, will normally be positioned within the body of the patient and an out-of-the body segment near the proximal end which, when the device is in use, will normally remain outside of the body of the patient,
  the in-the-body segment having on at least a portion thereof a lubricious coating material, the coating on at least a part of said coated portion being modified by an overcoating whereby a gradient of lubricity along the length of said coated portion of the in-the-body segment portion is provided.

* * * * *

UNITED STATES PATENT AND TRADEMARK OFFICE
CERTIFICATE OF CORRECTION

PATENT NO. : 5,902,631

DATED : May 11, 1999

INVENTOR(S) : Lixiao Wang et al

It is certified that error appears in the above-identified patent and that said Letters Patent is hereby corrected as shown below:

Col. 3, line 64, after the word "thereof" insert -- . --;

Col. 5, line 36, delete "±0.2" and insert -- 1 ±0.2 --;

Signed and Sealed this

Eighteenth Day of April, 2000

*Attest:*

Q. TODD DICKINSON

*Attesting Officer*  *Director of Patents and Trademarks*